United States Patent
Tanaka et al.

[11] Patent Number: 6,068,989
[45] Date of Patent: May 30, 2000

[54] METHOD AND DRY ANALYTICAL ELEMENT FOR DETERMINATION OF BICARBONATE ION IN LIQUID

[75] Inventors: Hideaki Tanaka; Yoshikazu Amano, both of Saitama, Japan

[73] Assignee: Fuji Photo Film Co., Ltd., Kanagawa, Japan

[21] Appl. No.: 09/387,117

[22] Filed: Aug. 31, 1999

[51] Int. Cl.[7] .............................. C12Q 1/32; C12Q 1/00; C12Q 1/48

[52] U.S. Cl. .................... 435/26; 435/4; 435/15; 564/80; 564/84; 564/92; 564/97; 422/50; 422/68.1

[58] Field of Search ................... 435/26, 4, 15, 435/283.1; 564/80, 84, 92, 97; 422/50, 68.1

[56] References Cited

FOREIGN PATENT DOCUMENTS 9916897  4/1999  WIPO .

*Primary Examiner*—Louise N. Leary
*Attorney, Agent, or Firm*—McAulay Nissen Goldberg & Kiel, LLP

[57] ABSTRACT

This invention provides a reagent composition for the determination of bicarbonate ion capable of measuring in a wide determination range in visible light region which comprises a combined substrate of thioNAD(P)H and NAD(P)H for a coupled enzymes of phosphoenolpyruvate carboxylase and malate dehydrogenase.

6 Claims, 2 Drawing Sheets

METHOD AND DRY ANALYTICAL ELEMENT FOR DETERMINATION OF BICARBONATE ION IN LIQUID

BACKGROUND OF THE INVENTION

This invention relates to a method and a dry analytical element for the determination of bicarbonate ion existing in a liquid sample. The method and dry analytical element are particularly effective for the determination of bicarbonate ion in a sample in clinical assay, such as blood or urine, which requires rapidity and high accuracy.

A conventional method for the determination of bicarbonate ion is of measuring the partial pressure of carboxylic acid in a liquid and hydrogen ion concentration (pH) by using electrodes. The concentration of bicarbonate ion can be determined by calculating from the above values. However, the method is disadvantageous in the simultaneous measurement of the partial pressure of carboxylic acid and pH of the liquid.

Another conventional method is of utilizing the conversion of bicarbonate ion into carbon dioxide in acidic conditions, and measuring the volume of the evolved carbon dioxide. In general, a large scale equipment is necessary for measuring the volume of gas accurately, and accordingly, this method is disadvantageous to the measurement of a large number of samples.

In order to solve the above disadvantages, some enzyme methods were developed.

The enzyme method disclosed in Japanese Patent KOKAI 4-210599 utilizes the following reactions,

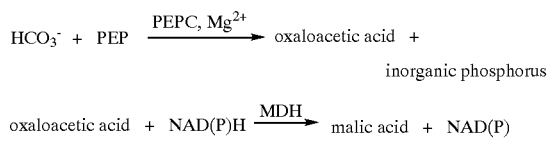

and bicarbonate ion is determined by measuring the decrease of absorption at 340 nm of NAD(P)H. In the above formulas, PEPC is phosphoenolpyruvate carboxylase, PEP is phosphoenolpyruvic acid, MDH is malate dehydrogenase, NADH is nicotinamide adenine dinucleotide in reduced form, NADPH is nicotinamide adenine dinucleotide phosphate in reduced form, and NAD and NADP are their oxidized forms, respectively.

The method disclosed in Japanese Patent KOKAI 4-248997 uses phosphoenolpyruvate carboxykinase instead of PEPC.

However, the above methods have following problems. First, since the absorbance at 340 nm is measured, the analyzer to be used must be equipped with an ultraviolet light source and detecting system therefor. As a result, the analyzer has a large scale, and is expensive. Second, since the absorbance of NAD(P)H at 340 nm is great, it is difficult to incorporate a necessary amount of NAD(P)H for converting the whole oxaloacetic acid produced in the above reaction into malic acid from first, by considering reaction rate. As a result, the determination range is narrow. Third, the above great absorbane problem can be avoided by changing the measuring wave length to a range of lower absorbance, such as 380 nm, and incorporating a sufficient amount of NAD(P)H. However, the measurement becomes unstable there due to the spectrum being not flat but oblique.

Moreover, blood samples are sometimes hemolyzed. Once hemolysis occurs, carbonic anhydrase eluted out of blood cell converts bicarbonate ion in blood into carbon dioxide. This brings a minus error on measurement. A countermeasure therefor is to add acetazolamide which is an inhibitor of carbonic anhydrase (Japanese Patent KOKAI 4-210599). However, acetazolamide has a difficulty in handling due to its irritation against eye and skin, and high price is also a problem.

SUMMARY OF THE INVENTION

An object of the invention is to provide a reaction system capable of measuring bicarbonate ion in a liquid by using a visible light source, in the presence of a sufficient substrate concentration, by a compact apparatus, with a wide determination range, rapidly, simply and stably, and to provide an analytical element therefor.

Another object of the invention is to provide a reaction system capable of resolving the minus error caused by hemolysis upon measuring bicarbonate ion in a blood sample by a safe and inexpensive means, and to provide an analytical element therefor.

The present invention provides a method for the determination of bicarbonate ion in a liquid which has achieved the first object, which uses phosphoenolpyruvate carboxylase and malate dehydrogenase wherein thioNAD(P)H and NAD(P)H are used as substrated of malate dehydrogenase, and a dry analytical element into which the above reagent system is incorporated.

The present invention also provides a method for the determination of bicarbonate ion in a liquid which has achieved further the second object, which comprises as above and further incorporating benzenesulfonamide or a compound having benzenesulfonamide structure of which one or two hydrogen atoms of the benzene ring were substituted into the reagent system.

In the above reaction system, reaction proceeds as follows:

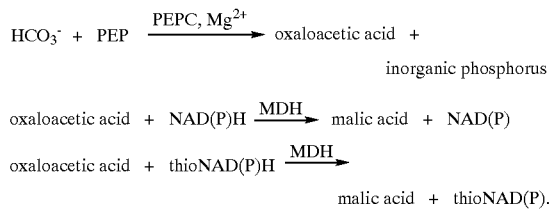

Since thioNAD(P)H has an absorption peak at 400 nm, a visible light source and detection system can be used. In the case of thioNAD(P)H alone, since the absorbance is high, the determination range becomes narrow. However, this phenomenon can be avoided by combining NAD(P)H at a prescribed ratio. Although it is uncertain how competitive reaction proceeds between thioNAD(P)H and NAD(P)H, as a result of measuring as to samples containing bicarbonate ion in various concentration, surprisingly, it was found that bicarbonate ion can be determined in a wide range with good reproducibility.

Moreover, the inventors investigated various materials in order to obtain a material having carbonic anhydrase inhibition activity at least comparable with acetazolamide and nevertheless having no problem in handling, and as a result, they found that benzenesulfonamide and the derivatives as above meet the object.

DETAILED DESCRIPTION OF THE INVENTION

Figure 1:
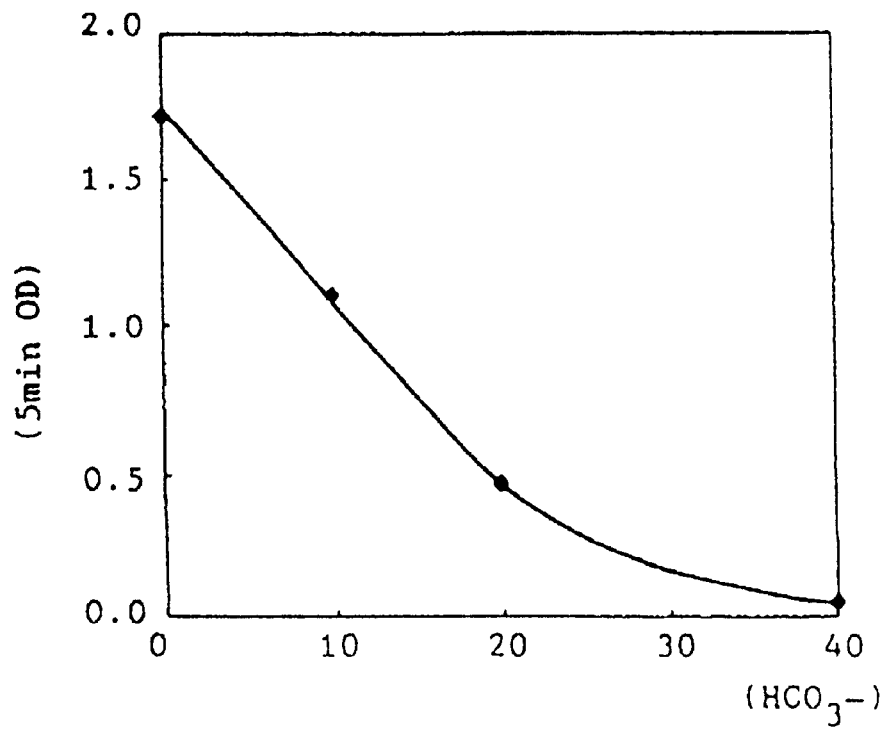
FIG. 1 is a graph indicating a relationship between bicarbonate ion concentration and optical density of reaction solution obtained in Example 1 using a mixture of thioN-ADH and NADH as the substrate.

Phosphoenolpyruvate carboxylase applicable to the invention functions to produce oxaloacetic acid from phosphoenolpyruvic acid, and includes EC4.1.1.31, EC4.1.1.32, EC4.1.1.38 and EC4.1.1.49. However, the presence of GDP is necessary for EC 4.1.1.32, inorganic phosphorus is necessary for EC 4.1.1.38, and ADP is necessary for EC 4.1.1.49, respectively.

As malate dehydrogenase, there are EC 1.1.1.37, EC 1.1.1.38, EC 1.1.1.39, EC 1.1.1.40, EC 1.1.1.83 and EC 1.1.99.16. The malate dehydrogenase applicable to the invention functions to produce malic acid from oxaloacetic acid, and includes EC 1.1.1.37 and EC 1.1.99.16.

The measuring reagent composition of the invention also contains substrates of the above coupled enzymes. The substrate of phosphoenolpyruvate carboxylase includes phosphoenolpyruvic acid and derivatives thereof on which the enzyme can act. The substrate of malate dehydrogenase used in the invention is a combination of thioNADH (thionicotinamide adenine dinucleotide) in reduced form or thioNADPH (thionicotinamide adenine dinucleotide phosphate) in reduced form and NADH (nicotinamide adenine dinucleotide) in reduced form or NADPH (nicotinamide adenine dinucleotide phosphate). ThioNAD(P)H is the same as NAD(P)H except that —$CONH_2$ in nicotinamide group is changed to —$CSNH_2$. ThioNAD(P)H is commerically available, and for example, sold by Sigma Chemical Co. A suitable molar ratio of thioNAD(P)H/NAD(P)H is 1/0.05–1/2, preferably 1/0.1–1/1, more preferably 1/0.2–1/0.7.

In the case of determining the bicarbonate ion concentration of a blood sample, it is preferable to incorporate carbonic anhydrase inhibitor into the reagent system. Applicable carbonic anhydrase inhibitors are acetazolamide, derivatives thereof, benzenesulfonamide, derivatives thereof and the like, and benzenesulfonamide and derivatives thereof found by the inventors are preferred. The derivatives of benzenesulfonamide have benzenesulfonamide structure of which one or two hydrogen atoms of the benzene ring were substituted. Illustrative of the substituents are hydroxyl group, amino group, halogen (fluorine, chlorine, bromine, iodine) atoms, nitro group, amide group, sulfonic group, carboxyl group, sulfonamide group, methyl group, ethyl group, propyl group, aminomethyl group, aminoethyl group, aminopropyl group, hydroxymethyl group, hydroxyethyl group, hydroxypropyl group, phosphate group, methoxy group, ethoxy group, and the like. Preferable substituents are amino group, halogen atoms, sulfonamide group, methyl group, aminoethyl group and the like. Examples of preferable benzenesulfonamide derivatives are p-toluenesulfonamide, 1-chlorobenzene-2,4-disulfonamide, 4-(2-aminoethyl) benzenesulfonamide, and the like, and p-toluenesulfonamide and 4-(2-aminoethyl) benzenesulfonamide are particularly preferable because of having excellent safety against skin and eye.

The measuring reagent composition may contain other components, such as known enzyme activators (e.g. $Mg^{2+}$), stabilizer, pH buffer (e.g. trishydroxymethylaminomethane), and the like.

A suitable amount of phosphoenolpyruvic acid is about 1.5 to 10 moles, preferably about 2 to 5 moles per 1 mole bicarbonate ion.

A suitable enzyme concentration is, in the case of rate assay, about 50 to 2,000 U/L, preferably about 100 to 1,000 U/L, for phosphoenolpyruvate carboxylase and about 1,000 to 50,000 U/L, preferably 2,000 to 20,000 U/L, for malate dehydrogenase. In the case of end point assay, a suitable phosphoenolpyruvate carboxylase concentration is about 2,000 to 200,000 U/L, preferably about 3,000 to 100,000 U/L, and a suitable malate dehydrogenase concentration is about 2,000 to 300,000 U/L, preferably about 5,000 to 200,000 U/L. A suitable amount of the sum of thioNAD(P)H and NAD(P)H is about 1 to 10 moles, preferably about 1.5 to 5 moles per one mole of $HCO_3^-$. A suitable ratio of phosphoenopyruvate carboxylase/malate dehydrogenase is about 1 to 1/20, preferably about 1 to 1/10.

The amount of carbonic anhydrase inhibitor is 0.1 mM or moe, and it can be added up to its solubility, i.e. soluble upper limit. The more amount of the inhibitor exhibits the greater inhibition against carbonic anhydrase. A preferably pH of its aqueous solution is about 8. In the case of a dry analytical element, a suitable content is about 5 to 2,000 mg/m², preferably about 50 to 1,000 mg/m². When the content is too great, deposition occurs.

As can be seen from the reaction formulas, it is possible that phosphoenolpyruvate carboxylase and phosphoenolpyruvic acid are first mixed with a bicarbonate ion solution, and thereafter, malate dehydrogenase and thioNAD(P)H and NAD(P)H are mixed with the reaction solution. However, it is convenient that a solution containing both enzymes and a solution containing both substrates are mixed with a bicarbonate ion solution. The reaction is carried out at a pH of about 6 to 10, preferably the optimum pH±1 of both enzymes, at 20 to 40° C., e.g. 37° C., for 1 to 15 minutes.

The measuring reagent composition of the invention can be used for the dry analysis as well as the wet analysis.

A preferable dry analytical element used in the dry analysis comprises three or more layer construction composed of a water-impermeable support and at least two water-permeable layers.

The support can be a water-impermeable light-transmissive support used for a conventional known dry analytical element, and includes a transparent film or sheet made of polyethylene terephthalate, polycarbonate of bisphenol A, polystyrene, cellulose ester, such as cellulose diacetate, cellulose triacetate and cellulose acetate propionate, or the like. The thickness of the support is usually in the range of about 50 μm to about 1 mm, preferably from about 80 μm to about 300 μm. The support may be provided with an undercoating layer on its surface in order to strengthen the adhesion of the reagent layer laminated thereon. Instead of the undercoating layer, the surface of the support may be treated by a physical activation, such as, glow discharge or corona discharge or by a chemical activation.

The water-permeable layers are reagent layer, light-blocking layer, adhesive layer, spreading layer, water absorption layer, and the like, described later.

On the support, the reagent layer is provided directly or through other layer(s) such as the undercoating layer. The reagent layer is a water-absorptive water-permeable layer wherein at least a part the aforementioned reagent composition is dispersed substantially uniformly in a hydrophilic polymer binder.

The hydrophilic polymer usable as the binder in the reagent layer is a natural or synthetic hydrophilic polymer having a swelling ratio in the range of about 1.5 to about 20, preferably from about 2.5 to about 15 at a water absorption at 30° C. Illustrative of the hydrophilic polymer are gelatins, such as acid-treated gelatin and deionized gelatin, gelatin derivatives, such as phthalated gelatin and hydroxyacrylate-graft gelatin, agarose, pullulan, pullulan derivatives, polyacrylamide, polyvinyl alcohol and polyvinylpyrrolidone.

The reagent layer may be a crosslinked (cured) layer to a certain degree by adding a crosslinking agent. Illustrative of the crosslinking agents are known vinyl sulfonyl crosslinking agents, such as 1,2-bis(vinylsulfonyl acetamide)ethane and bis(vinylsulfonylmethyl)ether, aldehydes and the like for gelatin, aldehydes, epoxy compounds having 2 glycidyl groups, and the like for methallyl alcohol copolymers.

A suitable dry thickness of the reagent layer is about 1 μm to about 100 μm, preferably about 3 μm to about 30 μm. The reagent layer is preferably transparent.

A light-blocking layer can optionally be provided on the reagent layer. The light-blocking layer is a water-permeable layer wherein light-absorptive or light-reflecting (called "light-blocking" collectively) particles are dispersed in a small amount of hydrophilic polymer having a film-forming ability as a binder. The light-blocking particles block the color of the sample spotted on the spreading layer described later, particularly the red color of hemoglobin in the case of whole blood samples, when a detectable change, such as color change or coloration, produced in the re agent layer is measured from the side of the light-transmissive support by reflection photometry. This layer also functions as a light-reflecting layer or a background layer. Illustrative of light-reflecting particles are titanium dioxide particles which are microcrystalline particles in rutile typ e, anatase type or brookite type having a particle size of about 0.1 μm to about 1.2 μm, barium sulfate particles and aluminum particles or microflakes, and illustrative of light-absorptive particles are carbon black, gas black and carbon microbeads. Preferred particles are titanium dioxide particles and barium sulfate particles, and anatase type titanium dioxide par tides are particularly preferred. The hydrophilic polymer binder having a film-forming ability includes the foregoing hydrophilic polymers usable for the reagent layer, weakly hydrophilic regenerated cellulose and cellulose acetate. Preferable hydrophilic polymers are gelatins, gelatin derivatives and polyacrylamide. A known curing agent (crosslinking agent) may be added to the gelatin or a gelatin derivative. The light-blocking layer may be formed by applying an aqueous solution of a hydrophilic polymer wherein light-blocking particles are suspended followed by drying. Instead of providing the light-blocking layer, the light-blocking particles may be incorporated in the spreading layer described layer.

An adhesive layer may be provided on the reagent layer or an optional layer, such as the light-blocking layer, in order to join the spreading layer. The adhesive layer is preferably composed of a hydrophilic polymer which can join the spreading layer thereby to integrate respective layers upon moistened or absorbing water to swell. Illustrative of the hydrophilic polymers usable for the production of the adhesive layer are the aforementioned hydrophilic polymers usable for the production of the reagent layer. Preferable ones are gelatin, gelatin derivatives and polyacrylamide. A suitable dry thickness of the adhesive layer is, in general, about 0.5 μm to about 20 μm, preferably about 1 μm to about 10 μm. The adhesive layer may also be provided on other layer(s) in order to improve adhesive force between other layers, in addition to the reagent layer. The adhesive layer can be formed by applying an aqueous hydrophilic polymer solution, to which a surfactant or the like is optionally added, onto the support, the reagent layer or the like by a known method.

The porous spreading layer may be a woven fabric spreading layer disclosed in U.S. Pat. No. 4,292,272, U.S. Pat. No. 4,783,315, etc., such as, plain weaves including broad cloth and poplin, a knitted fabric spreading layer disclosed in EP 0 162 302 A, etc., such as tricot, double tricot or milanese, a spreading layer made of a woven fabric or knitted fabric etched by an alkaline etching solution disclosed in Japanese Patent KOKAI 1-172753, a spreading layer made of organic polymer fiber pulp-containing paper disclosed in U.S. Pat. No. 5,215,716, a nonfibrous isotropic porous spreading layer, such as a membrane filter (blushed polymer layer) disclosed in U.S. Pat. No. 3,992,158, a continuous microspaces-containing porous layers where polymer particulates, glass particulates or diatomaceous earth are dispersed in a hydrophilic polymer binder, or a continuous microspaces-containig porous layer where polymer particulates are joined so as to contact with each other at a point by using a polymer adhesive which does not swell in water (three-dimensional lattice structure layer).

Two or more spreading layers may be incorporated. For example, two or more porous layers which are joined by an adhesive disposed in spots, such as disclosed in Japanese Patent KOKAI 61-4959, 62-138756, 62-135757 or 62-138758.

A spreading controller, such as a hydrophilic polymer may be incorporated into the spreading layer in order to control spreading ability. Various reagents or a part of reagent(s) may also be incorporated for the purpose of accelerating object detecting reaction or reducing or inhibiting interfering reaction(s).

A suitable thickness of the spreading layer is 20 to 200 μm, preferably 50 to 170 μm, more preferably 80 to 150 μm.

Physical activation treatment represented by glow discharge or corona discharge disclosed in U.S. Pat. No. 4,783,315 may be provided at least one side of the woven fabric, knitted fabric or paper used as the porous spreading layer. The woven fabric, knitted fabric or paper may be treated with degreasing by washing with water, or impregnating with a surfactant or a hydrophilic polymer. By providing the fabric or paper with one or more of the above treatment, the fabric or paper is rendered hydrophilic, and the adhesive force to the layer located on the underside, i.e. near the support, can be increased.

A water absorption layer may be provided between the support and t he reagent layer. The water absorption layer is mainly composed of a hydrophilic polymer which absorbs water to swell, and it absorbs the water of aqueous liquid sample which reaches the surface of this layer. In the case of whole blood sample, it accelerates permeation of blood plasma component into the reagent layer. The hydrophilic polymer usable for the water absorption layer can be selected from the aforementioned ones usable for the reagent layer. Preferred hydrophilic polymers for the water absorption layer are, in general, gelatin, a gelatin derivative, polyacrylamide and polyvinyl alcohol, particularly the aforementioned gelatins and deionized gelatin, and the aforementioned same gelatins as the reagent layer are the most preferable. The dry thickness of the water-absorption layer is about 3 μm to about 100 μm, preferably about 5 μm to about 30 μm. The coating weight of the water-absorption layer itself is about 3 g/m² to about 100 g/m², preferably about 5 g/m² to about 30g/m². By incorporating a pH buffer, basic polymer or the like described later into the water absorption layer, pH upon use (conducting analytical operations) can be adjusted. Moreover, a known mordant, polymer mordant, etc. maybe incorporated into the water absorption layer.

The reagent composition can be incorporated into the reagent layer or any other one or more layers. For example, it can be incorporated into the reagent layer or the spreading layer. All of the reagent composition can be incorporated into one layer. In this case, components reacting with each other are incorporated separately, and the latter component is incorporated so that reaction does not proceed before measurement, such as by dispersing in alcohol and then applying the dispersion.

The blood sample applicable to the invention may be any one of whole blood, plasma, serum or the like.

EXAMPLES

The following solutions were prepared.

| (A) Enzyme Solution | |
|---|---|
| Tris buffer | 75 mM (pH 8) |
| PEPC (EC 4.1.1.31) | 3 U/ml |
| MDH (EC 1.1.1.37) | 30 U/ml |
| $Mg^{2+}$ | 19.8 mM |
| (B) Substrate Solution | |
| Tris buffer | 75 mM (pH 8) |
| PEP | 6.75 mM |
| ThioNADH | 0.45 mM |
| NADH | 0.23 mM |
| (C) $HCO_3^-$ Solution | |
| | 0 mM |
| | 10 mM |
| | 20 mM |
| | 40 mM |

At 37° C., 20 μl of the $HCO_3^-$ solution was put in a cell, and 2 μl of the enzyme solution and 1 μl of the substrate solution were added to the cell, successively. The absorbance at 400 nm of each mixed solution was measured for 5 minutes, and a calibration curve was prepared using the absorbance after 5 minutes. The results are shown in FIG. 1.

From the above results, it can be seen that the determination of bicarbonate ion is possible at a measuring wavelength of 400 nm.

Comparative Example 1

Instead of the substrate solution (B), the following substrate solution was prepared.

| (D) Substrate Solution | |
|---|---|
| Tris buffer | 75 mM (pH 8) |
| PEP | 6.75 mM |

| (D) Substrate Solution | |
|---|---|
| ThioNADH | 0.45 mM |

Figure 2:
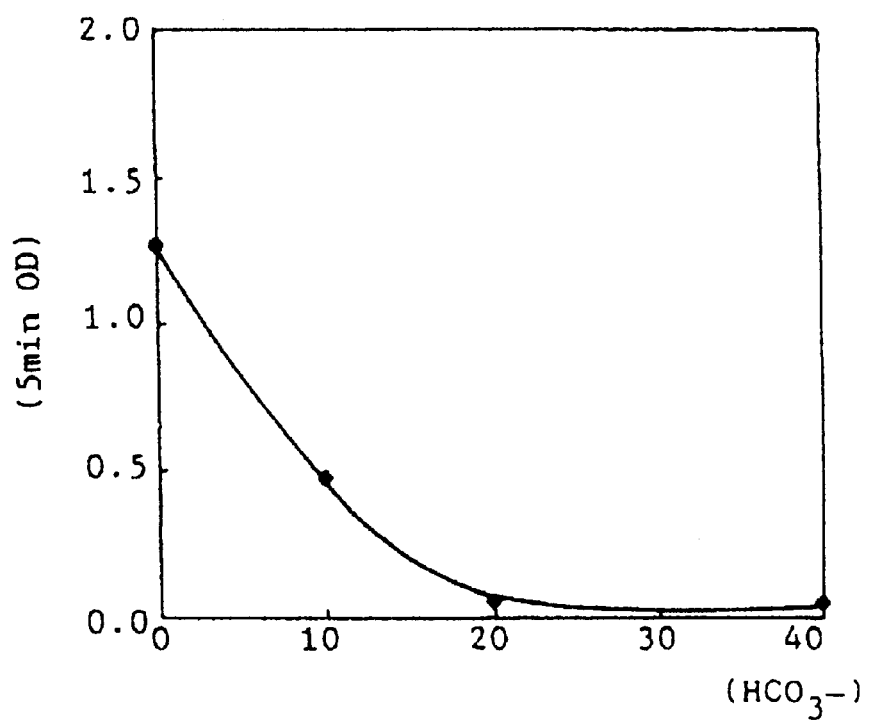
FIG. 2 is a graph indicating a relationship between bicarbonate ion concentration and optical density of reaction solution obtained in Comparative Example 1 using thioN-ADH as the substrate.

Using the substrate solution (D), bicarbonate ion was determined similar to Example 1. The calibration curve thus obtained is shown in FIG. 2.

From the above results, it can be seen that the determination range is considerably narrowed unless NADH coexists.

Example 2

An aqueous solution was applied onto a clear PET base 180 μm in thickness so as to become the following coating amounts, followed by drying.

| | |
|---|---|
| ThioNADH | 2 g/m² |
| NADH | 1 g/m² |
| MDH (EC 1.1.1.37) | 4,000 U/m² |
| Tris buffer | 4.85 g/m² |
| Polyoxyethylenenonylphenylether | 0.25 g/m² |
| Gelatin | 10 g/m² |

An aqueous solution was applied onto the above coating layer so as to become the following coating amounts, followed by drying.

| | |
|---|---|
| PEP | 6 g/m² |
| PEPC (EC 4.1.1.31) | 4,500 U/m² |
| $MgCl_2$ | 3 g/m² |
| Tris buffer | 4.85 g/m² |
| Polyoxyethylenenonylphenylether | 0.25 g/m² |
| Gelatin | 10 g/m² |
| Titanium dioxide | 3.65 g/m² |

A polyester knitted fabric was laminated to the above coating layer, and an aqueous solution containing polyvinyl alcohol and surfactant was applied thereto in order to control the spreading of sample solution.

The analytical element thus prepared was cut into pieces of about 1.3×1.4 cm, and set in a mount having an opening of 12 mm in diameter to complete analytical slides.

Each 10 μl of the $HCO_3^-$ solutions prepared in Example 1 was spotted onto 4 pieces of the above analytical slides, and measurement was carried out similar to Example 1. Then, similar results to Example 1 were obtained.

Comparative Example 2

An aqueous solution was applied onto a clear PET base 180 μm in thickness so as to become the following coating amounts, followed by drying.

| | |
|---|---|
| ThioNADH | 2 g/m² |
| MDH (EC 1.1.1.37) | 4,0000 U/m² |
| Tris buffer | 4.85 g/m² |
| Polyoxyethylenenonylphenylether | 0.25 g/m² |
| Gelatin | 10 g/m² |

Hereafter, conducting similar to Example 2, analytical slides were prepared, and measurements were carried out. Then, similar results to Comparative Example 1 were obtained.

Example 3

| | |
|---|---|
| $HCO_3^-$ | 35 mM |
| Tricine | 100 mM (pH 8) |
| One of carbonic anhydrase inhibitors (a)–(g) | 2 mM |
| Carbonic anhydrase | 230,000 U/L |

Figure 3:
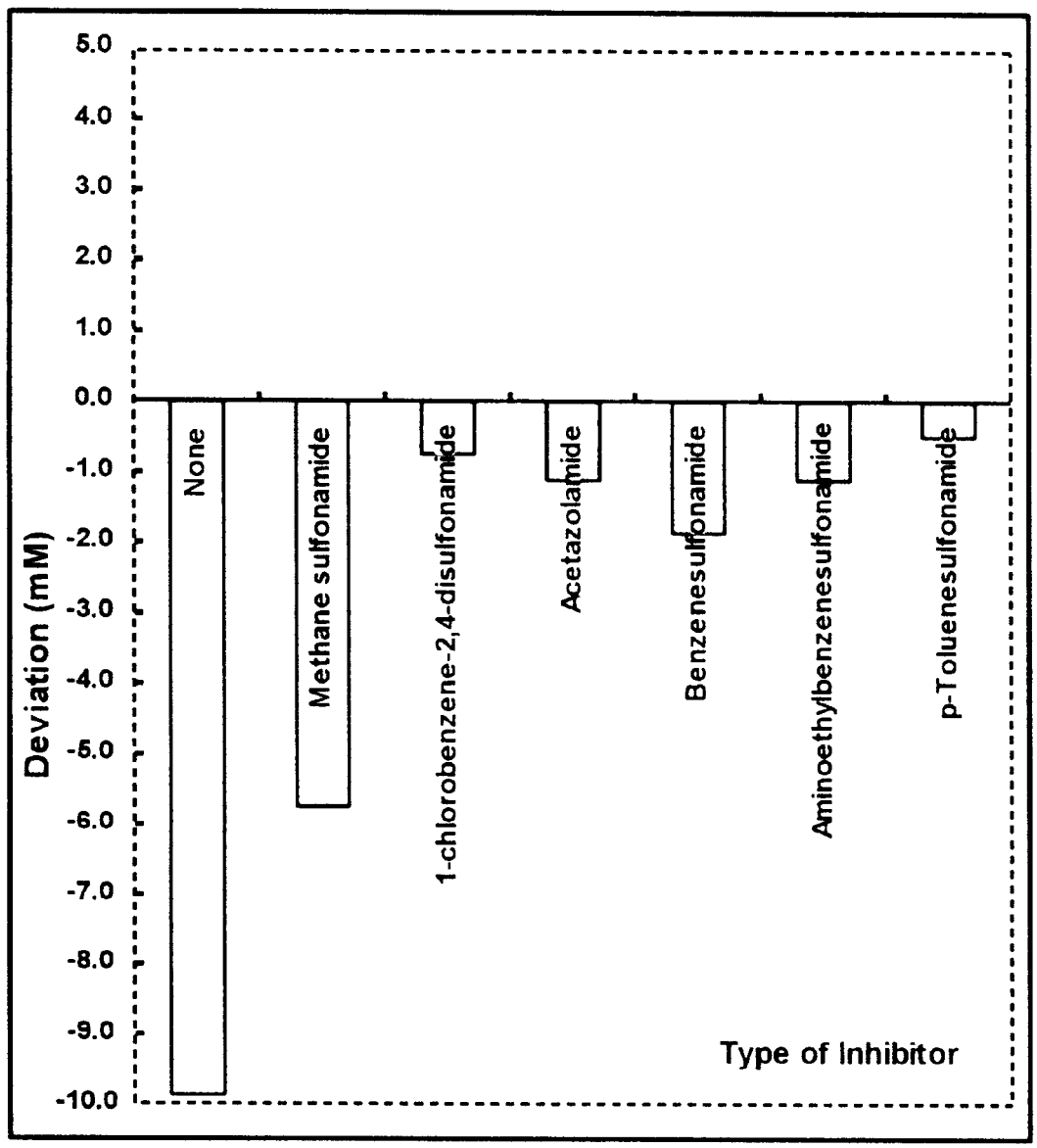
FIG. 3 is a graph indicating a result of measuring $HCO_3^-$ concentration of a $HCO_3^-$ solution containing carbonic anhydrase using various carbonic anhydrase inhibitors.

Carbon anhydrase inhibitor (a) None (b) Methanesulfonamide (c) 1-chlorobenzene-2,4-disulfonamide (d) Acetazolamide (e) Benzenesulfonamide (f) 4-(2-aminoethyl) benzenesulfonamide (g) p-toluenesulfonamide Hereafter, conducting similar to Example 1, the determination of bicarbonate ion was carried out. The results are shown in Table 1 and FIG. 3.

TABLE 1

| | Measured Value | | |
|---|---|---|---|
| | Carbonic Anhydrase | | Deviation |
| Inhibitor | Added | Not Added | (mM) |
| None | 24.3 | 34.2 | −9.9 |
| Methanesulfonamide | 28.0 | 33.8 | −5.8 |
| 1-chlorobenzene-2,4-disulfonamide | 37.8 | 38.5 | −0.7 |
| Acetazolamide | 36.9 | 38.0 | −1.2 |
| Benzenesulfonamide | 35.6 | 37.5 | −1.9 |
| 4-(2-aminoethyl)benzenesulfonamide | 36.0 | 37.1 | −1.1 |
| p-toluenesulfonamide | 35.8 | 36.3 | −0.5 |

From the above results, it can be seen that benzenesulfonamide and its derivatives can decrease the minus deviation caused by carbonic anhydrase effectively, and have a carbonic anhydrase inhibition ability comparable with or superior to acetazolamide.

What is claimed is:

1. A method for the determination of bicarbonate ion in a liquid phosphoenolpyruvate carboxylase and malate dehydrogenase thioNAD(P)H and NAD(P)H as substrates of malate dehydrogenase.

2. The method of claim 1 wherein the molar ratio of thioNAD(P)H/NAD(P)H is 1/0.05 to 1/2.

3. The method of claim 1 further comprising using benzenesulfonamide or a compound having benzenesulfonamide structure of which one or two hydrogen atoms of the benzene ring are substituted.

4. The method of claim 3 wherein the benzenesulfonamide or a compound having benzenesulfonamide structure of which one or two hydrogen atoms of the benzene ring are substituted is p-toluenesulfonamide or 4-(2-aminoethyl) benzenesulfonamide.

5. A dry analytical element for the determination of bicarbonate ion in a liquid which comprises at least two water-permeable layers lamianted onto a water-impermeable support, wherein the water-permeable layers as a whole contain phosphoenolpyruvate carboxylase, malate dehydrogenase, thioNAD(P)H and NAD(P)H.

6. The dry analytical element of claim 5 wherein the water-permeable layers further contain benzenesulfonamide or a compound having benzenesulfonamide structure of which one or two hydrogen atoms of the benzene ring are substituted.

* * * * *